United States Patent [19]

Prescher et al.

[11] Patent Number: 4,642,387

[45] Date of Patent: Feb. 10, 1987

[54] PROCESS FOR THE PRODUCTION OF 3-CYCLOHEXENE-1-CARBOXALDEHYDE

[75] Inventors: Guenter Prescher, Hanau; Andreas Grund, Darmstadt; Heinrich Petsch, Hanau; Georg Boehme, Rodenbach, all of Fed. Rep. of Germany

[73] Assignee: Degussa Aktiengesellschaft, Frankfurt, Fed. Rep. of Germany

[21] Appl. No.: 813,904

[22] Filed: Dec. 27, 1985

[30] Foreign Application Priority Data

Jan. 19, 1985 [DE] Fed. Rep. of Germany ....... 3501665

[51] Int. Cl.$^4$ .................... C07C 45/69; C07C 47/42
[52] U.S. Cl. .................................................. 568/446
[58] Field of Search ......................................... 568/446

[56] References Cited

U.S. PATENT DOCUMENTS 1,891,043 12/1932 Diels et al. ................. 568/446 X
1,944,732 1/1934 Diels et al. .................... 568/446

OTHER PUBLICATIONS

Hougen, et al, Chemical Process Principles, Part I (1954), 213.
Habeshaw et al., Chem. Abs., vol. 48 (1954) 7056(d).

*Primary Examiner*—Bernard Helfin
*Attorney, Agent, or Firm*—Beveridge, DeGrandi & Weilacher

[57] ABSTRACT

A continuous process for the production of 3-cyclohexene-1-carboxaldehyde by reaction of acrolein with butadiene at an elevated temperature and increased pressure is described in which good yields are obtained by establishing the weight ratio of the starting substances fed per time unit into a circulation reactor in relation to the reaction mixture circulated per time unit in the range of 1:5 to 1:60 and by carrying out a secondary reaction in successive reactors.

11 Claims, No Drawings

PROCESS FOR THE PRODUCTION OF 3-CYCLOHEXENE-1-CARBOXALDEHYDE

The present invention relates to a process for the production of 3-cyclohexene-1-carboxaldehyde.

It has been known for a long time, for example from O. Diels and K. Alder, Liebigs Ann. Chem. 460, 98 (1928) or from the British Pat. No. 1,024,012 and the British Pat. No. 309,911, that acrolein may be reacted with butadiene in a bomb tube or in an autoclave in a discontinuous method of operation to form 3-cyclohexene-1-carboxaldehyde. The reaction achieved according to this known process and the yields are not always satisfactory, since the $\alpha,\beta$-unsaturated aldehyde used as a starting compound as well as the conjugated olefin may be easily polymerized at a higher temperature. For one thing, the reaction discussed has a very exothermal nature, and on the other hand however, and in order to achieve a sufficiently high reaction speed, a reaction temperature of generally more than 90° C. must prevail. Since, in the case of these temperatures, the polymerization of the starting substances is already favored, it is necessary to exercise extreme caution in heating up for a discontinuous method of operation. This is true above all whenever considerable equimolar quantities of the reaction partners are made to react with one another since the danger of local, strong overheating may lead to an extremely violent reaction which can no longer be controlled.

Therefore, the proposal has been made to carry out the reaction in inert solvents or at low temperatures in, for example, benzol as a solvent in the presence of organo aluminum compounds as catalysts (see U.S. Pat. No. 3,067,233 and British Pat. No. 835,840).

The yields of 3-cyclohexene-1-carboxaldehyde achieved in the case of these processes however are generally moderate; moreover, the use of metal organic catalysts which are exceedingly easily flammable requires completely anhydrous starting substances and solvents which, in addition to the problem of recapturing of the solvent, requires considerable effort of technical measures.

A continuous process for the production of 3-cyclohexene-1-carboxaldehyde from butadiene and excess acrolein in a single reaction vessel is described in the British Pat. No. 689,568. In this process, as the initial material, a C4-cracking cut of only 60% butadiene content is used; the required reactor volume therefore becomes disproportionally great. Furthermore, 8% of residue are obtained. In addition, the other components contained in the crude butadiene as well as considerable quantities of excess acrolein must be separated and recycled or purified.

Therefore, even the previously mentioned continuous process is not suitable for the economic production of 3-cyclohexene-1-carboxaldehyde on a larger scale.

Accordingly, it is the object of the invention to provide a process for the production of 3-cyclohexene-1-carboxaldehyde by way of the Diels-Alder reaction of butadiene with acrolein at elevated temperature and increased pressure which is characterized by the fact that the reaction is carried out continuously in such a way that first of all one operates in a circulation reactor to which acrolein and butadiene are fed continuously at temperatures between 80° C. and 160° C., preferably between 100° C. and 130° C., whereby a part of the reaction mixture is guided in a circle and the weight ratio of the starting substances fed per time unit to the reaction mixture circulated per time unit amounts to 1:5 to 1:60. Subsequently, the reaction mixture leaving the circulation reactor, which mixture contains at least 50% by weight of 3-cyclohexene-1-carboxaldehyde, is fed to a second circulation reactor in which likewise a part of the reaction mixture is guided in a circle, whereby the ratio of the reaction mixture fed in per time unit from the first circulation reactor to the reaction solution circulated per time unit likewise amounts to 1:5 to 1:60, and in which the reaction is carried out at a temperature between 100° C. and 200° C. preferably at 110° C. to 150° C. The reaction solution leaving the second circulation reactor which has a content of at least 75% of 3-cyclohexene-1-carboxaldehyde is fed to a secondary reactor in which no circulation of the reaction mixture takes place and the temperature is in the range of 100° C.–240° C., preferably 140° to 170° C. Thereafter, the reaction mixture is distilled to obtain a fractionated manner.

The invention thus results in an advantageous solution of the problem, since for a considerable part of the reaction, a strong back mixing takes place with the product already formed which causes a precisely adjustable diluting effect as a result of the quantity of starting substances fed in. In order to achieve a complete reaction, the reaction is carried to its end in a secondary or after reactor without circulation which may be preceded by a second circulation reactor. According to the process of the invention conversion of up to about 98% and yields of more than 90% of 3-cyclohexene-1-carboxaldehyde are achieved, whereby the portion of polymeric substances or high boiling products as a rule does not surpass 1.5–3%, related to the substances used.

Suitable for the reaction is acrolein of technical quality which has a water content of about 3%; however, one may use just as well anhydrous acrolein or acrolein with higher water contents.

The mole ratio of acrolein and butadiene amounts generally to 0.5:1 to 2:1, preferably 0.9:1 to 1.1:1.

Generally, one uses reaction temperatures of 80°–200° C., preferably 100°–150° C. in loop reactors used as circulation reactors; in the secondary reactor the reaction temperature may amount to 100°–240° C., preferably 140°–170° C. The conversion reaction generally is carried out at a pressure resulting in the reactors as the sum of the partial pressure of the reaction participants which is very much lower because of the high back mixing with the product already formed than in the case of comparable continuous processes, and as a result of that leads to considerable advantages with regard to the apparatus. However, it is also possible to use a higher pressure, for example up to 200 bar.

Customarily, acrolein is stabilized against polymerization so that the reaction takes its course in the presence of the polymerization inhibitor. As polymerization inhibitors, customarily there may be used inhibitors such as, for example, hydroquinone. Related to the acrolein, their concentration amounts to 0.05–1, preferably 0.1 to 0.5% by weight.

In order to carry out the continuous process according to the invention, for example, one or two loop reactors connected in succession are suitable from which a part of the reaction mixture is conducted away and optionally again fed to the reactor after cooling of the reactor. Furthermore, feed lines are attached on the loop reactors for the starting substances or for the already partially reacted reaction solution and a discharge line is attached for the reaction product. The starting substances may be added to the reactor in such a manner that they are first mixed and afterwards the mixture is fed into the reactor. However, one may also proceed in such a way that the starting substances are introduced at different places into the loop reactor. Effectively, the feeding in of the starting substances takes place with good mixing with the reaction material according to customary methods which are either known or easily accessible to the skilled worker in the art. In the circulation reactors, the weight ratio of the substances fed per time unit to the reaction mixture guided in a circle per time unit amounts to at least 1:5, preferably 1:10, to 1:60.

The reaction mixture leaving the first circulation reactor contains in relation to the sum of the substances used at least 50% by weight, especially 60–80% by weight of 3-cyclohexene-1-carboxaldehyde. For completing the reaction, one then feeds the reaction mixture leaving the circulation apparatus to a secondary reactor in which no reaction mixture is guided in a circle.

According to the invention, it is particularly advantageous to feed the reaction mixture leaving the circulation reactor first to a second circulation reactor which is operated under reaction conditions previously mentioned, and then only thereafter the reaction mixture leaving the second circulation reactor is fed to the secondary (after) reactor for the purpose of completion of the reaction, which mixture, related to the sum of the raw substances used, has a content of 3-cyclohexene-1-carboxaldehyde of at least 75, preferably 85–95% by weight.

As a secondary reactor, preferably a pipe reactor is used which essentially consists of one or more bundled pipes. In an advantageous embodiment of the process according to the invention, as a result of the ratio of reaction mixture flowing through the secondary reactor to the reactor cross section, care is being taken of the fact that a back mixing will be suppressed to the greatest extent. In the secondary reactor, the reaction is carried out at a temperature of 100°–240° C., preferably 140°–170° C. The reaction mixture leaving the secondary reactor, beside a content of 90–93% 3-cyclohexene-1-carboxaldehyde has approximately 1.5% of water, has only about 2% dimers and 2% high boiling matter and polymers beside the converted starting material.

The 3-cyclohexene-1-carboxaldehyde obtained by way of the process according to the invention is a valuable, intermediate product, for example, for the production of epoxide resins, odoriferous substances and pharmaceutically active substances.

It should be understood the circulation reactors and secondary reactors used according to the invention as described herein are of conventional design and any suitable apparatus of this type may be used for purposes of the invention as will be apparent to those skilled in the art.

The following examples serve to illustrate the present invention:

EXAMPLE 1

The conversion is carried out in a laboratory installation described below. Using a circulation reactor of 2.9 l content, a part of the reaction mixture is removed at the upper end of the reactor and after passing through a thermostatisized stretch is fed again by way of a pump to the reactor at the lower end. Acrolein and butadiene are mixed in the reactor prior to their entry and are fed on top of the reactor to the reactor mixture. A part of the reaction mixture corresponding to the feed is removed from the reactor and is fed to the after connected pipe reactor which has a length of 10 m and a volume of 1.1 l. The reaction mixture leaving the pipe reactor is released to standard pressure and is processed by distillation. In order to carry out the reaction, every hour 317 g (96%) of acrolein, which contains 0.3% hydroquinone, and 307 g of butadiene (99%) (mole ratio 1:1.04) are added. The medium total dwell time amounts to about 5.5 hours. The temperature in the loop reactor amounts to 130° C., in the secondary reactor to 150° C.; the pressure is maintained at 25 bar.

The reaction mixture leaving the circulation reactor contains 77.5% by weight of 3-cyclohexene-1-carboxaldehyde; the reaction mixture leaving the secondary reactor has a content of 92.5% of 3-cyclohexene-1-carboxaldehyde, which means a yield of 95.9% at an acrolein conversion of 96.9%. The content of polymers amounts merely to 2.3%.

The ratio of reaction mixture feed to circulated reaction mixture ranges to about 1:25.

EXAMPLE 2

As in Example 1, except however, with interposition of an additional circulation reactor with a volume of 2.8 l upstream from the secondary reactor, there is introduced on an hourly basis 278 g of acrolein stabilized with 0.3% of hydroquinone and 296 g of butadiene (mole ratio 1:1.13). The temperatures of the two circulation reactors amount to 120° C.; of the secondary reactor to 150° C.; the pressure is maintained at 25 bar. The content of 3-cyclohexene-1-carboxaldehyde in the reaction mixture after the first circulation reactor amounts to 77.6% by weight, after the second circulation reactor to 89.4% and after the secondary reactor to 93.6%. In the case of an acrolein conversion of 97.5%, there is obtained after the distillation at 15 mmHg/62° C. a yield of 93.7% 3-cyclohexene-1-carboxaldehyde. The residue amounts to less than 2%, related to the sum of the substances used. In both circulation reactors, the ratio of reaction mixture feed to circulated reaction mixture amounts to about 1:25 to 1:30.

EXAMPLE 3

As described in Example 1, there is used on an hourly basis 317 g of acrolein stabilized with 0.3% of hydroquinone and 300 g of butadiene (mole ratio 1:1.01). The temperature amount in loop 1 to 120° C., in loop 2 to 120° C. and in the secondary reactor to 150° C.

The contents of 3-cyclohexene-1-carboxaldehyde in the reaction mixture prior to loop 1 amounts to 76.9%, after the loop 2 to 86.4% and after the pipe reactor to 92.6%.

The conversion of acrolein amounts to 98.4%, the yield after distillation to 92.4% and the residual content of polymers to 1.9%.

EXAMPLE 4

(comparison example)

In a pipe reactor of 3.9 m length and a volume of 250 ml, at 130° C. there was introduced every hour 212 g of an equimolar mixture of acrolein stabilized with 0.3% hydroquinone and butadiene.

After about 12 hours, the pipe reactor was plugged up by insoluble polymer deposits, so that the experiment had to be discontinued.

Further variations and modifications will be apparent to those skilled in the art from the foregoing and are intended to be encompassed by the claims appended hereto.

We claim:

1. A process for the production of 3-cyclohexene-1-carboxaldehyde by reaction of acrolein with butadiene at an elevated temperature and increased pressure, comprising carrying out the reaction between acrolein and butadiene continuously in a first stage circulation reactor to which acrolein and butadiene are fed continuously at temperatures between 80° C. and 160° C., to form a reaction mixture, whereby a part of the reaction mixture is guided in a circle, in which the weight ratio of the feed acrolein and butadiene starting substances per time unit to the reaction mixture circulated per time unit amounts to 1:5 to 1:60, and guiding the reaction mixture leaving the first stage circulation reactor, which mixture contains at least 50% by weight of 3-cyclohexene-1-carboxaldehyde, to a secondary reactor in which no circulation of the reaction mixture takes place and in which the reaction is completed at 100° to 240° C., and the reaction mixture obtained is subsequently separated by fractional distillation.

2. The process as set forth in claim 1, wherein the temperature in the first stage is 100° to 130° C. and the temperature in the secondary reactor is 140° to 170° C.

3. A process for the production of 3-cyclohexene-1-carboxaldehyde by reaction of acrolein with butadiene at an elevated temperature and increased pressure, comprising carrying out the reaction between acrolein and butadiene continuously which acrolein and butadiene are fed continuously at temperatures between 80° C. and 160° C. to form a reaction mixture, whereby a part of the reaction mixture is guided in a circle, in which the weight ratio of the feed acrolein and butadiene together per time unit to the reaction mixture circulated per time unit amounts to 1:5 to 1:60, subsequently guiding the reaction mixture leaving the first stage circulation reactor, which mixture contains at least 50% by weight of 3-cyclohexene-1-carboxaldehyde, to second stage circulation reactor in which a part of the reaction mixture is guided in a circle, whereby the weight ratio of the reaction solution fed per time unit from the first stage circulation reactor to the reaction solution circulated per time unit amounts to at least 1:5, and carrying out the reaction in the second stage at a temperature between 100° C. and 200° C., the reaction solution leaving the second stage circulation reactor having a content of at least 75% of 3-cyclohexene-1-carboxaldehyde, feeding the reaction solution leaving the second stage to a secondary reactor in which no circulation of the reaction mixture takes place and in which the reaction is completed at 100° to 240° C., and subsequently separating the reaction mixture obtained by fractional distillation.

4. The process as set forth in claim 3, wherein the temperature is said first stage is 100° to 130° C. and the temperature in the second stage is 110° to 150° C.

5. The process as set forth in claim 3, wherein the reaction in the secondary reactor takes place at 140° to 170° C.

6. The process as set forth in claim 1, wherein there is used acrolein with a water content of maximally 7% by weight.

7. The process as set forth in claim 1, wherein the mole ratio between acrolein and butadiene used amounts to 0.5:1 to 2:1.

8. The process as set forth in claim 1, wherein polymerization inhibitors are present in the acrolein.

9. The process as set forth in claim 3, wherein there is used acrolein with a water content of maximally 7% by weight.

10. The process as set forth in claim 3, wherein the mole ratio between acrolein and butadiene used amounts to 0.5:1 to 2:1.

11. The process as set forth in claim 3, wherein polymerization inhibitors are present in the acrolein.

* * * * *